United States Patent
Zoromski et al.

(10) Patent No.: US 6,588,073 B1
(45) Date of Patent: Jul. 8, 2003

(54) MALE FASTENERS WITH ANGLED PROJECTIONS

(75) Inventors: Paula Kay Zoromski, Appleton, WI (US); Richard J. Schmidt, Roswell, GA (US); Mari-Pat Y. Von Feldt, Atlanta, GA (US); Brian Keith Nortman, Appleton, WI (US); Andrew Mark Long, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/637,307

(22) Filed: Aug. 11, 2000

(51) Int. Cl.[7] .............................................. A44B 18/00
(52) U.S. Cl. .............................. 24/446; 24/450; 24/452
(58) Field of Search ........................ 24/452, 442, 446, 24/449, 450; 604/391; 428/100

(56) References Cited

U.S. PATENT DOCUMENTS

| | | | |
|---|---|---|---|
| 4,680,838 A | | 7/1987 | Astl |
| 4,794,028 A | | 12/1988 | Fischer ........................ 428/100 |
| 4,794,674 A | | 1/1989 | Mintel et al. |
| 4,846,815 A | | 7/1989 | Scripps |
| 4,984,339 A | * | 1/1991 | Provost et al. ................. 24/442 |
| 5,058,247 A | * | 10/1991 | Thomas et al. ................ 24/448 |
| 5,116,563 A | * | 5/1992 | Thomas et al. .............. 156/242 |
| 5,208,952 A | | 5/1993 | Mintel et al. |
| 5,325,569 A | * | 7/1994 | Goulait et al. ................. 24/448 |
| 5,383,872 A | | 1/1995 | Roessler et al. ............. 604/391 |
| 5,392,498 A | * | 2/1995 | Goulait et al. ................. 24/446 |
| 5,537,720 A | * | 7/1996 | Takizawa et al. .............. 24/442 |
| 5,586,371 A | * | 12/1996 | Thomas ......................... 24/306 |
| 5,720,740 A | * | 2/1998 | Thomas ......................... 24/448 |
| 5,781,969 A | * | 7/1998 | Akeno et al. .................. 24/442 |
| 5,858,515 A | | 1/1999 | Stokes et al. |
| 5,875,527 A | | 3/1999 | Lacey et al. |
| 5,884,374 A | * | 3/1999 | Clune ........................... 24/446 |
| 5,887,320 A | * | 3/1999 | Provost ......................... 24/442 |
| 5,897,545 A | * | 4/1999 | Kline et al. .................... 24/304 |
| 5,953,797 A | * | 9/1999 | Provost et al. ................. 24/304 |
| 5,961,761 A | | 10/1999 | Heindel et al. .............. 156/163 |
| 6,061,881 A | * | 5/2000 | Takizawa et al. .............. 24/446 |
| 6,131,251 A | * | 10/2000 | Provost ......................... 24/452 |

FOREIGN PATENT DOCUMENTS

| | | |
|---|---|---|
| EP | 276970 A2 * | 8/1988 |
| EP | 0 476 992 B1 | 7/1995 |

\* cited by examiner

*Primary Examiner*—James R. Brittain
(74) *Attorney, Agent, or Firm*—Pauley Petersen Kinne & Erickson

(57) ABSTRACT

A male component of a male and female fastening system, such as a hook and loop fastener, that can remain fastened to a female component under high levels of shear force. The male component has a backing material with projections extending from the backing material at an angle toward the direction of fastener force. The combination of the male component with a standard female loop component results in a secure fastening system. The combination of the male component with a standard female loop component is particularly beneficial when used in absorbent articles.

8 Claims, 3 Drawing Sheets

MALE FASTENERS WITH ANGLED PROJECTIONS

FIELD OF THE INVENTION

This invention is directed to a male component of a male and female fastener, such as a hook and loop fastener. More particularly, the male component has projections angled toward the direction of fastener shear force.

BACKGROUND OF THE INVENTION

A number of fastening systems, such as diaper fastening systems, incorporate a male and female fastener, such as a hook and loop system, for easy fastening and release. The male component typically includes a flat plastic hook backing with a number of protruding hooks that engage with a number of loops on a female component. The hooks protruding from the hook backing of the male component typically project perpendicularly to the flat hook backing, and thus perpendicularly to the direction of fastener shear force. When the fastening system is fastened and shear force acts upon the fastening system, the perpendicular projections pull toward the direction of fastener force. As the projections are pulled, any hook portions on the projections are also pulled, which can result in the hooks releasing the loops, with the fastening system becoming unfastened as a final result. Furthermore, perpendicular projections often produce red-marking and irritation if brought into contact with a person's skin, such as an infant's skin in contact with a hook component of a diaper fastening system.

There is a need or desire for a male component of a male and female fastener that can remain fastened to a female component under high levels of shear force.

There is also a need or desire for a male component of a male and female fastener that reduces or eliminates the occurrence of red-marking and/or irritation if brought into contact with a person's skin.

SUMMARY OF THE INVENTION

The present invention is directed to a male component of a male and female fastener, such as a hook and loop fastener, having projections angled toward the direction of fastener shear force applied by the male component and acting on the female component. The angled projections can apply a greater amount of shear force to the loops than perpendicular projections without disengaging from the loop, thereby resulting in a more secure fastening system. Furthermore, the angled projections can reduce skin irritation often caused by perpendicular projections.

The angled projections can have an engaging portion at the free end or can be free of hooks, or a combination of hook and non-hook type angled projections can be located on the male component. An entire surface of the male component can be covered with angled projections, or alternatively, the surface can have a combination of perpendicular projections and angled projections. The angled projections can be shorter in length than the perpendicular projections, such that the angled projections only participate in the shear function and do not cause skin irritation.

The angled projections can be formed from a mold designed to produce such projections, or from a mold specially shaped to produce angled projections when the male component is removed from the mold. Alternatively, the angled projections can be formed by using two or more polymers side-by-side in a mold, such that the projections become angled as the polymers cool due to differential shrinkage of the polymers.

With the foregoing in mind, it is a feature and advantage of the invention to provide a male component of a male and female fastener, such as a hook and loop fastener, that can remain fastened to a female component under high levels of shear force.

It is another feature and advantage of the invention to provide a male component of a male and female fastener that reduces or eliminates the occurrence of red-marking and/or irritation if brought into contact with a person's skin.

It is yet another feature and advantage of the invention to produce a male and female fastening system that includes the above male component.

DEFINITIONS

Figure 1:
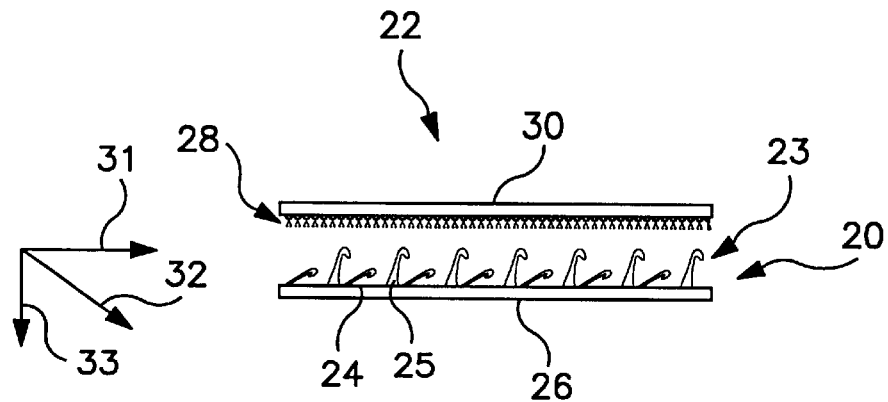
FIG. 1 is a side view of a male component and a female component prior to engagement with one another.

Within the context of this specification, each term or phrase below will include the following meaning or meanings.

"Angled projection" refers to a projection in a male component that is angled toward a direction of fastener shear force, i.e., is non-perpendicular to a male component backing.

"Direction of fastener force" refers to a force exerted by the male component on the female component while the components are engaged (e.g. while the article embodying the fastener is being worn). The fastener force is a vector force having a shear force component and a perpendicular force component.

"Engaging portion" refers to a part of a fastening component that is suitably shaped to enable the fastening component to engage or secure itself to a complementary fastening component. Examples of engaging portions include J-shaped hooks, and flat-topped hook portions atop projections having a diameter narrower than the flat top.

"Perpendicular direction" or "perpendicular force direction" refers to a direction normal (90 degrees) to a backing material or other reference surface. The perpendicular direction is perpendicular to the shear direction, defined below.

"Perpendicular force" refers to forces that tend to produce an opposite pulling motion in a perpendicular direction between two bodies' planes.

"Polymers" include, but are not limited to, homopolymers, copolymers, such as for example, block, graft, random and alternating copolymers, terpolymers, etc. and blends and modifications thereof Furthermore, unless otherwise specifically limited, the term "polymer" shall include all possible geometrical configurations of the material. These configurations include, but are not limited to isotactic, syndiotactic and atactic symmetries.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Resilient" refers to a material that is flexible, compressible and re-formable.

"Shear force" refers to forces that tend to produce an opposite but parallel sliding motion between two bodies' planes.

"Shear direction" or "shear force direction" refers to a direction parallel to a backing material or other reference surface undergoing shear force.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

The present invention is directed to a male component of a male and female fastening system, such as a hook and loop fastener, that can remain fastened to a female component under high levels of shear force. The invention is also directed to a hook and loop fastener that includes the male component and a female component. The male component includes projections that extend from a backing material at an angle toward the direction of fastener shear force. The geometry of the male component can also reduce or eliminate the occurrence of red-marking and/or irritation if brought into contact with a person's skin.

This male component is particularly suitable for use in fastening systems on disposable absorbent articles in which the fastener force has a significant shear force component during use. Examples of such suitable articles include diapers, training pants, feminine hygiene products, incontinence products, other personal care or health care garments, including medical garments, or the like.

As shown in FIG. 1, a male component 20 and a female component 22 can be brought together to be releasably attached, or releasably engaged, to one another. The male component 20 has a number of individual projections 23 protruding from a resilient hook backing material 26. Similarly, the female component 22 has a number of individual loops 28 protruding generally perpendicularly from a resilient loop backing material 30. The individual projections 23 and the individual loops 28, when brought into contact with one another, engage with one another, with the projections 23 latching onto the loops 28, until forcibly separated, thereby pulling the projections 23 out of the loops 28.

The individual loops 28 of the female component 22 can be needled, stitched or otherwise projected through the loop backing material 30. The loop backing material 30 can suitably be made from a nonwoven material. The individual loops 28 can suitably be made from a fibrous nonwoven web such as a spunbond nonwoven web, or a staple fiber carded web. An example of a suitable nonwoven web is disclosed in U.S. Pat. No. 5,858,515 to Stokes, et. al, and is hereby incorporated by reference. Alternatively, the individual loops 28 can be made of yarn or tow. Once the loops 28 have been formed, fibers forming the loops can be anchored in place by bonding the fibers to the loop backing material 30 with heat and/or adhesives or any other suitable: means. Such suitable female components 22 are available from Velcro, USA, of Manchester, N.H.

Figure 2:
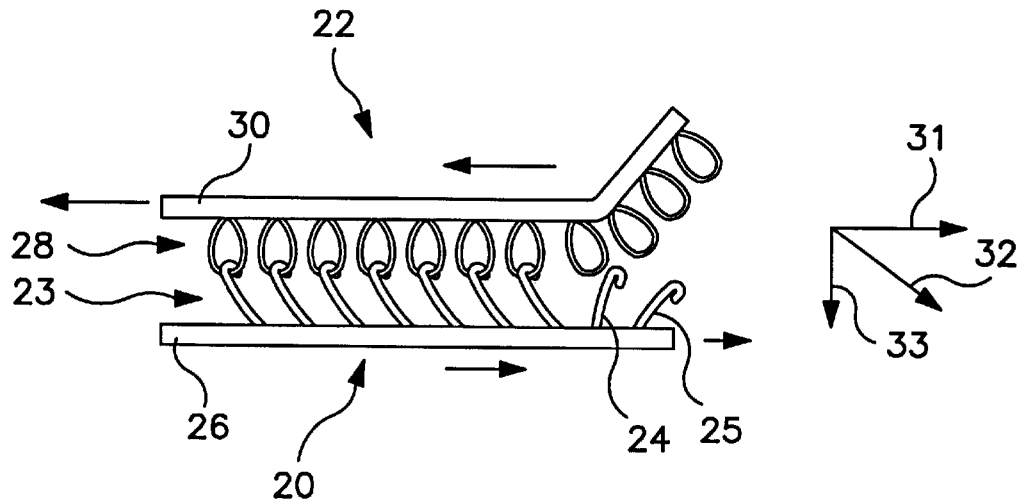
FIG. 2 is a side view of a male component in partial engagement with a female component.
Figure 6:
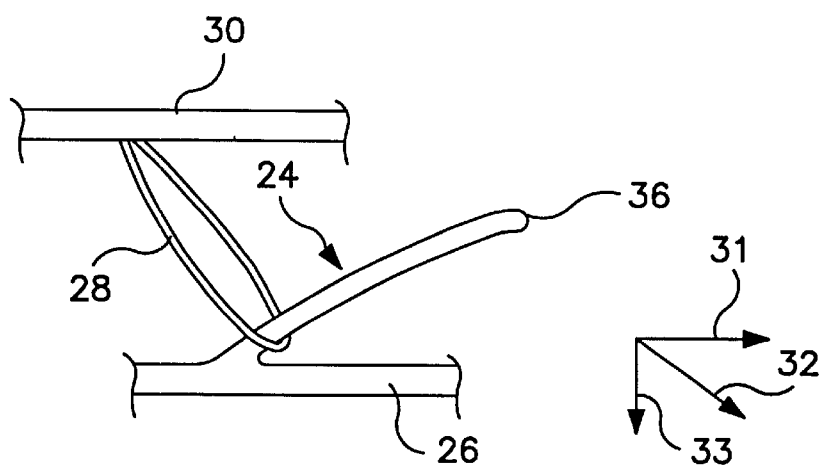
FIG. 6 is an end view of an angled projection on a male component.

At least some of the individual projections 24 of the male component 20 of the present invention are angled, at least in part, toward the direction of fastener shear force. As used herein, the term "direction of fastener shear force" refers to a shear component of a direction, i.e., the direction of fastener force, which a male component 20 applies to a mating female component 22 when the male and female components are engaged and under tension. FIG. 2 shows the male component 20 and the female component 22 of FIG. 1 in an engaged position under tension, wherein part of the components 20 and 22 are undergoing disengagement. The direction of fastener force is indicated by arrow 32 in FIGS. 1 and 2. The direction of fastener shear force is indicated by arrow 31 in FIGS. 1 and 2. The direction of a perpendicular force component of the fastener force is indicated by arrow 33 in FIGS. 1 and 2. The fastener shear force is in direct opposition to shear force exerted by the female component 22 against the male component 20. If the angled projections 24 are flexible, the loops 28 of the female component 22 may bend the angled projections 24 in a direction opposite the direction of fastener shear force, as shown in FIG. 2. Alternatively, the angled projections 24 can be relatively stiff, thereby latching the loop 28 between the projection 24 and the hook backing material 26, as shown in FIG. 6.

Figure 3:
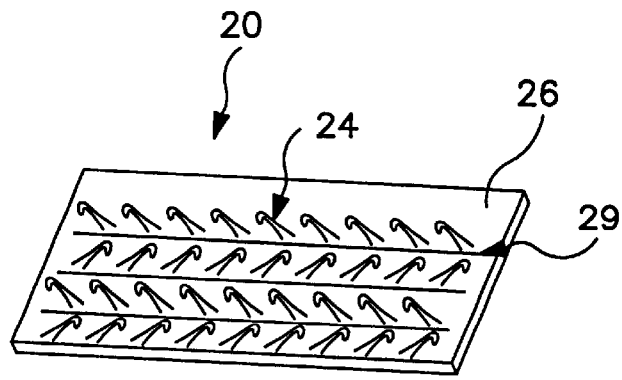
FIG. 3 is a plan view of a male component.

The angled projections 24 can handle a greater amount of shear force exerted by the female component 22 than typical perpendicular projections 25 because the female component 22 must overcome a greater amount of fastener shear force when the projections 24 are angled toward the direction of fastener shear force. Male components 20 having angled projections 24 thereby result in a more secure fastening system. To address opposite directions of fastener shear force, depending on the direction in which the female component is separated from the male component, angled projections 24 are suitably located in opposite directions, as illustrated in FIG. 3. Furthermore, the angled projections 24 reduce the number of sharp ends poking a wearer by pointing sharp ends away from the wearer, and can thus reduce skin irritation often caused by perpendicular projections 25.

All of the individual projections 23 of the male component 20 can be angled toward the direction of fastener force or, alternatively, some of the individual projections 23 can be angled projections 24, angled toward the direction of fastener force and some of the individual projections 23 can be perpendicular projections 25, roughly perpendicular to the hook backing material 26 (and roughly perpendicular to the direction of fastener shear force). A combination of angled projections 24 and perpendicular projections 25 is shown in FIGS. 1 and 2. Individual projections 24 that are angled non-perpendicular to the hook backing 26 are suitably at an angle of about 20 degrees to about 70 degrees with respect to the hook backing material 26 (and the direction of fastener shear force), more suitably at an angle of about 30 degrees to about 60 degrees, most suitably at an angle of about 35 degrees to about 55 degrees. Individual projections 25 that are roughly perpendicular to the backing material 26 and direction of shear force, are suitably at an angle of about 80 degrees to about 100 degrees with respect to the hook backing material 26.

Figure 4:
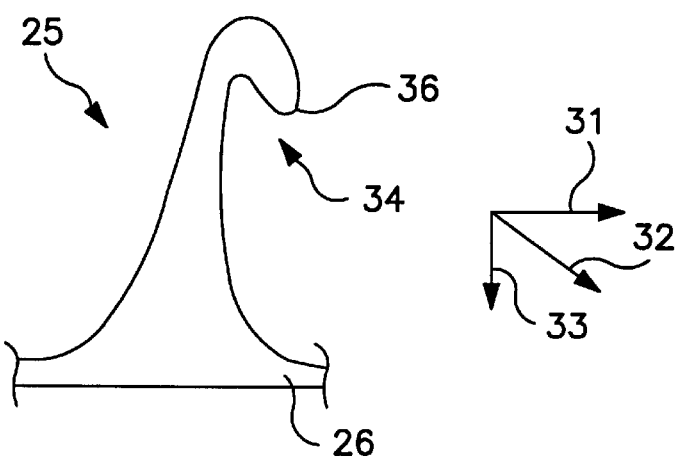
FIG. 4 is a side view of a roughly perpendicular projection on a male component.
Figure 5:
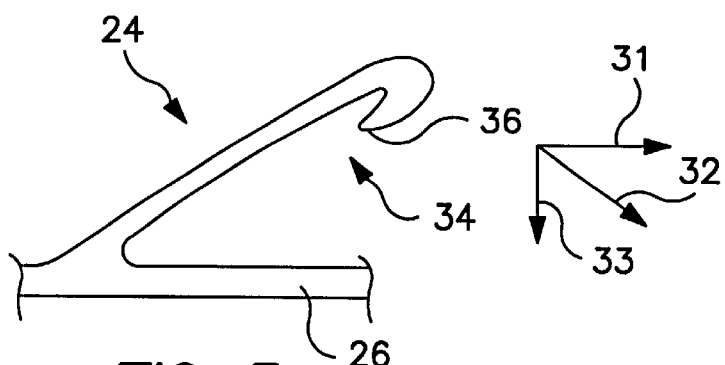
FIG. 5 is an end view of an angled projection on a male component.

Each of the roughly perpendicular projections 25 suitably has an engaging portion 34 at a free end 36 of the projection 25, as is commonly used in the art, and is shown in FIG. 4. However, not all of the angled projections 24 need to have an engaging portion 34 at a free end 36 of the projection 24. Some or all of the angled projections 24 can have engaging portions 34, as shown in FIG. 5, while some or all of the angled projections 24 may lack an engaging portion 34, as shown in FIG. 6. Furthermore, some or all of the angled projections 24 having engaging portions 34 can have a flat-topped engaging portion 34, shown in FIG. 7, as opposed to the J-shaped engaging portion 34 shown in FIG. 5. The angled projections 24 can be shorter in length than the roughly perpendicular projections 25, as shown in FIG. 1, thereby providing the benefit of handling a great amount of shear force but without protruding far enough to cause skin irritation.

Figure 7:
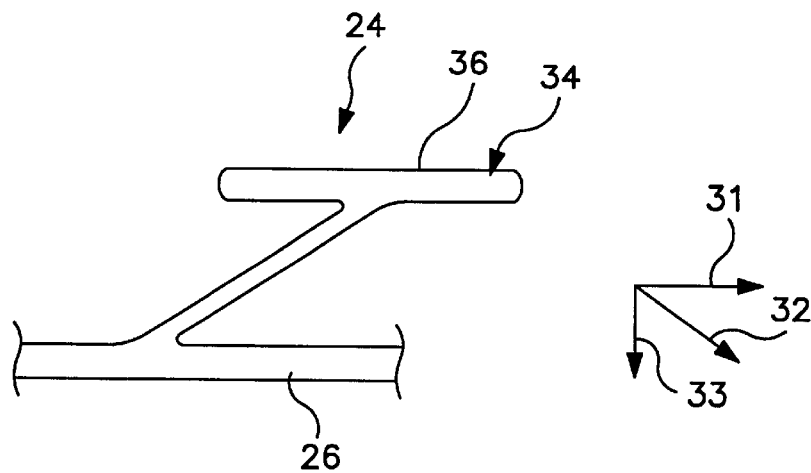
FIG. 7 is an end view of an angled projection on a male component.
Figure 8:
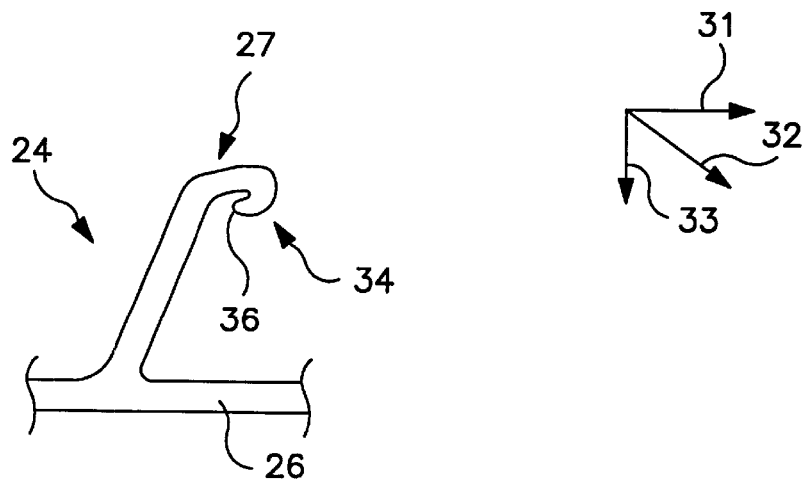
FIG. 8 is a side view of an angled projection on a male component.

The angled projections 24 can be more angled along a small portion, such as at one end 27, as shown in FIG. 8, or along a substantial length of the projection 24, as shown in FIGS. 5–7. The term "substantial length," as used herein, refers to the full length of the projection 24, not including the engaging portion 34.

The male components 20 of the present invention can generally have between about 16 and about 930 projections 23 per square centimeter, or between about 124 and about 470 hooks projections 23 per square centimeter, or between about 155 and about 310 projections 23 per square centimeter. The projections 23 suitably have a height of from about 0.00254 centimeter (cm) to about 0.19 cm, or from about 0.019 cm to about 0.070 cm. The projections 23 are suitably molded or extruded from a thermoplastic polymer selected from polyamides, polyesters, polyolefins (e.g. polyethylene, polypropylene, polybutene, ethylene copolymers, propylene copolymers, or butene copolymers), a thermoplastic elastomer, or another suitable material. Likewise, the hook backing material 26 can be made of any of these or any other suitable materials. The hook backing material 26 generally has a thickness in a range of between about 0.4 millimeter (mm) and about 5 mm, suitably in a range of between about 0.6 mm and 2 mm, resulting in a total basis weight of the male component 20 in a range of from about 20 grams per square meter to about 70 grams per square meter.

The projections 23 can be spatially arranged in rows with spacers 29 between the rows, as shown in FIG. 3. These spacers 29 can be in the form of bumps, ridges, depressions, or any other suitable distortion made in or added to the hook backing material 26. These spacers 29 improve the overall flexibility of the hook backing material 26 by providing areas of lower density among the individual projections 23 where the hook backing material 26 can easily bend to conform to a wearer's body as the body moves. Furthermore, the spacers 29 also improve the flexibility of individual projections 23 by providing room for the projections 23 to bend in response to applied pressure. Alternatively, the rows can be separated by a flat surface. Also, as mentioned, the projections 23 are suitably arranged such that a plurality of the projections 23 face one way and a plurality of the projections 23 face an opposite way in order to compensate for directions of fastener forces in opposite directions.

The male component 20 of the present invention can be made according to a method similar to that disclosed in U.S. Pat. No. 4,794,028 issued to Fischer, hereby incorporated by reference. More particularly, a heat softened synthetic resin, namely any of the aforementioned suitable polymers, is extruded and shaped between a pair of rollers. One of the rollers has a plurality of projection-forming mold cavities about its periphery within which the projections 23 of the hook component 20 are formed. Once the projections 23 are cooled and at least partially solidified in the mold cavities, the projections 23 are removed or stripped from the roller, remaining integral with the hook backing material 26, without a need to open the cavities. When the projections 23 are removed from the cavities on the roller, the projections 23 can either be molded in the shape of the angled projections 24, or can then be bent into the angled projections 24. As indicated, the individual projections 24 can be co-formed with the hook backing material 26.

Figure 9:
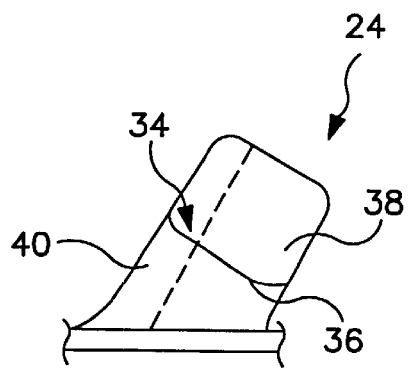
FIG. 9 is a side view of an angled projection made of two different polymers.

Alternatively, this method can be modified by using at least two different polymers 38 and 40 aligned side-by-side along a length of the projection mold. When the polymers 38 and 40 are heated, all of the polymers should be heat softened. The polymers 38 and 40 should be carefully chosen, such that one polymer 38 shrinks more than the other 40 or others during the cooling process. Thus, when the polymers 38 and 40 cool, the polymer 38 that shrinks more lowers the projection 24 toward the hook backing material while the polymer 40 that shrinks less forms a surface away from the hook backing material 26, as shown in FIG. 9.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A male and female fastening system comprising a male component and a female component;
   the female component including a loop backing and a plurality of loops protruding from it;
   the male component including a hook backing and a plurality of hooks and projections protruding from the hook backing, each hook having a first longitudinal surface portion protruding from the hook backing at an angle of about 20 degrees to about 70 degrees relative to the hook backing with an engaging portion protruding from an end of the hook on a second longitudinal surface portion of the hook wherein the engaging portion does not protrude from the end of the hook on the first longitudinal surface portion of the hook, and each projection having an end with a surface at an angle of about 80 degrees to about 100 degrees relative to the hook backing.

2. The male and female fastening system of claim 1, wherein a plurality of the projections each comprises an engaging portion at one end.

3. The male and female fastening system of claim 1, wherein the first longitudinal surface portion of each hook protrudes from the hook backing at an angle of about 30 degrees to about 60 degrees relative to the hook backing.

4. The male and female fastening system of claim 1, wherein the first longitudinal surface portion of each hook protrudes from the hook backing at an angle of about 35 degrees to about 55 degrees relative to the hook backing.

5. The male and female fastening system of claim 1, wherein a substantial length of each hook is at an angle of about 20 degrees to about 70 degrees relative to the hook backing.

6. The male and female fastening system of claim 1, wherein a substantial length of each hook is at an angle of about 30 degrees to about 60 degrees relative to the hook backing.

7. The male and female fastening system of claim 1, wherein a substantial length of each hook is at an angle of about 35 degrees to about 55 degrees relative to the hook backing.

8. The male and female fastening system of claim 1, wherein a plurality of the hooks are shorter than a plurality of the projections.

\* \* \* \* \*